United States Patent
Rieber et al.

(10) Patent No.: US 8,457,375 B2
(45) Date of Patent: Jun. 4, 2013

(54) VISUALIZATION METHOD AND IMAGING SYSTEM

(75) Inventors: Johannes Rieber, München (DE); Markus Rossmeier, Bamberg (DE)

(73) Assignee: Siemens Aktiengesellschaft, München (DE)

( * ) Notice: Subject to any disclaimer, the term of this patent is extended or adjusted under 35 U.S.C. 154(b) by 271 days.

(21) Appl. No.: 12/888,523

(22) Filed: Sep. 23, 2010

(65) Prior Publication Data
US 2011/0075912 A1 Mar. 31, 2011

(30) Foreign Application Priority Data
Sep. 25, 2009 (DE) .......... 10 2009 043 069

(51) Int. Cl.
*G06K 9/00* (2006.01)
(52) U.S. Cl.
USPC ............ 382/128; 345/629; 378/8; 378/4
(58) Field of Classification Search
USPC ................. 382/128, 130; 345/629
See application file for complete search history.

(56) References Cited

U.S. PATENT DOCUMENTS

| | | | |
|---|---|---|---|
| 6,148,095 A | 11/2000 | Prause et al. | |
| 7,343,195 B2 | 3/2008 | Eichler et al. | |
| 7,630,472 B2 * | 12/2009 | Tsuyuki et al. | 378/8 |
| 7,936,945 B2 * | 5/2011 | Soinio et al. | 382/275 |
| 8,108,029 B2 * | 1/2012 | Rasche | 600/424 |
| 2001/0029334 A1 * | 10/2001 | Graumann et al. | 600/437 |
| 2004/0097805 A1 * | 5/2004 | Verard et al. | 600/428 |
| 2005/0018885 A1 * | 1/2005 | Chen et al. | 382/128 |
| 2005/0256398 A1 * | 11/2005 | Hastings et al. | 600/423 |
| 2006/0036167 A1 | 2/2006 | Shina | |
| 2006/0262139 A1 * | 11/2006 | Rahn | 345/629 |
| 2007/0030946 A1 * | 2/2007 | Tsuyuki et al. | 378/8 |
| 2007/0055142 A1 * | 3/2007 | Webler | 600/425 |
| 2009/0281418 A1 * | 11/2009 | Ruijters et al. | 600/424 |

FOREIGN PATENT DOCUMENTS

| | | |
|---|---|---|
| DE | 102004011154 B3 | 11/2005 |
| DE | 10200503747 A1 | 2/2007 |
| DE | 102005039657 A1 | 3/2007 |
| DE | 102006061178 A1 | 6/2008 |
| WO | WO 2006076409 A2 | 7/2006 |
| WO | WO 2007002685 A2 | 1/2007 |
| WO | WO 2007113705 A1 | 10/2007 |

\* cited by examiner

*Primary Examiner* — Chan S Park
*Assistant Examiner* — Iman K Kholdebarin

(57) ABSTRACT

A method is provided for visualization of hollow organs of a patient. An x-ray image dataset of the hollow organ is recorded and registered. A number of individual x-ray images are recorded during a movement of an instrument with a data capture unit through the hollow organ, with each individual x-ray image featuring time information. Datasets of a data capture unit of an instrument is recorded during the movement of the instrument, with each dataset featuring time information. Position of the instrument is determined based on the individual x-ray images by an image recognition algorithm. The datasets of the data capture unit and the position of the instrument is spatially assigned based on the time information of the datasets of the data capture unit and the individual x-ray images. The datasets of the data capture unit is jointly displayed with the x-ray image dataset.

18 Claims, 2 Drawing Sheets

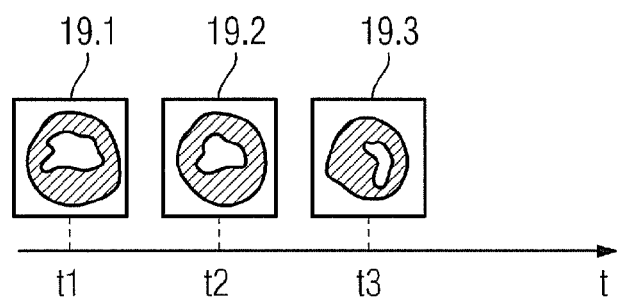
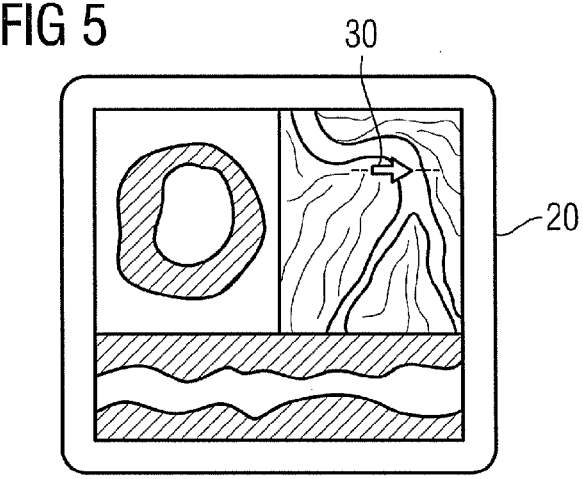
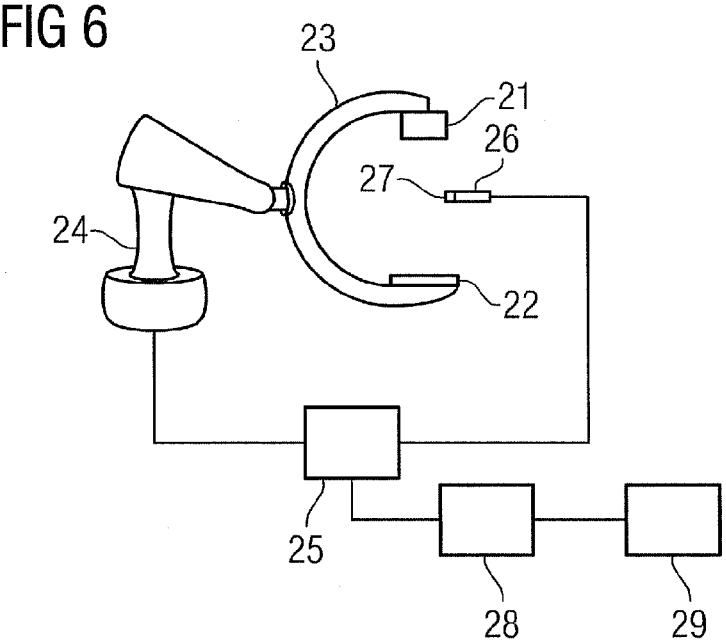

VISUALIZATION METHOD AND IMAGING SYSTEM

CROSS REFERENCE TO RELATED APPLICATIONS

This application claims priority of German application No. 10 2009 043 069.5 filed Sep. 25, 2009, which is incorporated by reference herein in its entirety.

FIELD OF THE INVENTION

The invention relates to a method for visualizing hollow organs of a patient as well as to a medical imaging system for carrying out such a method.

BACKGROUND OF THE INVENTION

In angiography, for visualization of vascular systems, radiopaque contrast media is injected into the vascular system and the outflow of contrast media is then documented under x-ray control. In this case naturally only information about the lumen of the vessel can be provided since the vessel wall is not contrasted by the contrast medium used. The advantage of angiography lies in its ability to provide high-quality information. In order to obtain further information about the structure of the vessel wall or structures adjacent to it, such as stents or other types of implants for example, other invasive technologies such as intravascular ultrasound (IVUS) or optical coherence tomography for example are needed. Additional physiological information is obtained using so-called pressure wire technology or intravasal Doppler wire technology.

The disadvantage of these technologies is that they frequently lack orientation in the vascular system. Spatial orientation is carried out indirectly using anatomical landmarks (such as plaques, outlets of side branches etc.). Another possibility is the use of magnetic navigation and positioning systems (GIVUS). In these systems the IVUS transducer can be equipped with a special sensor and then the position can be determined very precisely using a magnetic field generator. The disadvantage of this method is the high financial outlay for the navigation system and the additional equipping of the IVUS catheter with the position sensors, so that application for clinical routines is too costly.

Intravasal diagnostic methods are typically applied in such a way that an instrument such as a catheter or a Doppler/pressure wire is brought to the most distal position and is then withdrawn (automatically or manually) from this position. In such cases the examination data obtained is recorded digitally.

SUMMARY OF THE INVENTION

The object of the present invention is to provide a method which, with modern catheter or wire-based examination techniques, makes a simple spatial orientation in the vascular system possible; a further object of the invention is to provide a suitable device for carrying out the method.

The object is inventively achieved by a method for visualizing hollow organs of a patient and by a medical imaging system in accordance with the independent claims. Advantageous embodiments of the invention are the subject matter of the associated dependant claims in each case.

The inventive method for visualizing hollow organs of a patient comprises the following steps:

Recording and registering an x-ray image dataset of the hollow organ,

Recording a number of individual x-ray images while the instrument, especially a catheter, is moving with a data capture unit through the hollow organ, with each individual x-ray image featuring time info nation, Recording datasets of the data capture unit during the movement of the instrument, with each dataset having time information, Determining the position of the instrument on the basis of the individual x-ray images by means of an image recognition algorithm, Spatial assignment of the datasets of the data capture unit and the position of the instrument on the basis of the time information of the datasets of the data capture unit and the individual x-ray images, Joint visualization of the datasets of the data capture unit with the x-ray image dataset.

The inventive method provides the option of visualizing a vascular system of a patient simultaneously in overview and in detail and thus for example providing a doctor with all information needed for a precise diagnosis. In such cases the inventive method can be carried out automatically or at least semi-automatically in a simple manner and with little effort.

In accordance with an embodiment of the invention a segmentation of the hollow organs is carried out on the basis of the x-ray dataset. The segmentation enables the position of the instrument to be determined more quickly and with fewer errors.

In accordance with a further embodiment of the invention the instrument is formed by a catheter. This catheter here can for example involve a catheter embodied for intravascular ultrasound. As well as a catheter the instrument can also be formed by a pressure wire or by a Doppler wire.

Advantageously, for an especially high-quality display of vascular systems, the x-ray image dataset of the hollow organ is formed by an angiography x-ray image dataset.

Expediently the position of the instrument is detected by means of an edge detection algorithm. Image processing software for edge detection is known and is well suited to determining a position of x-ray-transparent objects in an x-ray image.

Advantageously the position is detected automatically.

According to a further embodiment of the invention the time infotination is formed by information about the time of the respective recording. In this way the respective image or dataset is stored together with a time relating to its recording relative to a reference time. As an alternative the recording sequence can also be stored instead of the time of the recording.

According to a further embodiment of the invention the individual x-ray images and/or of the x-ray image dataset are recorded triggered, especially EKG-triggered. This is especially suitable for enabling comparable images of the hollow organ during organ movements, e.g. heartbeat or breathing, i.e. images in which the hollow organ is located at the same position, to be recorded.

Advantageously for simple detection of the position on the individual x-ray images, the catheter has a catheter tip which is not transparent to x-rays.

Expediently the data capture unit is formed by an imaging unit. As an alternative the data capture unit can also be formed by an ultrasound measurement unit or a pressure measurement unit or a lipid measurement unit or a coherence tomography unit.

In an advantageous manner the method is carried out automatically. Suitable for especially automatic execution of the method is a medical imaging system featuring an angiography x-ray system with an x-ray source and an x-ray detector, and featuring a catheter system with a catheter and a data capture unit and also featuring a control system, an imaging unit and a display unit.

BRIEF DESCRIPTION OF THE DRAWINGS

The invention as well as further advantageous embodiments in accordance with features of the dependant claims will be explained below in greater detail with reference to schematically represented exemplary embodiments in the drawing, without the invention being restricted to these exemplary embodiments. The figures show:

FIG. 4 a view of a sequence of IVUS images during the movement of the catheter;

FIG. 5 a combined display of the angiography dataset and the associated IVUS images; and FIG. 6 a view of a medical imaging system suitable for the method.

DETAILED DESCRIPTION OF THE INVENTION

X-ray imaging and especially angiography allow spatial arrangements of vascular systems to be especially well visualized, but the corresponding vessel walls are only little visible. Other measurement methods, especially intravascular ultrasound imaging (IVUS) or optical coherence tomography (OCT), offer good visualizations of the vessel walls but have the disadvantage of overview and spatial orientation being deficient. The invention contains a method which connects x-ray imaging with a further measurement method such that a parallel display is available.

Figure 1:
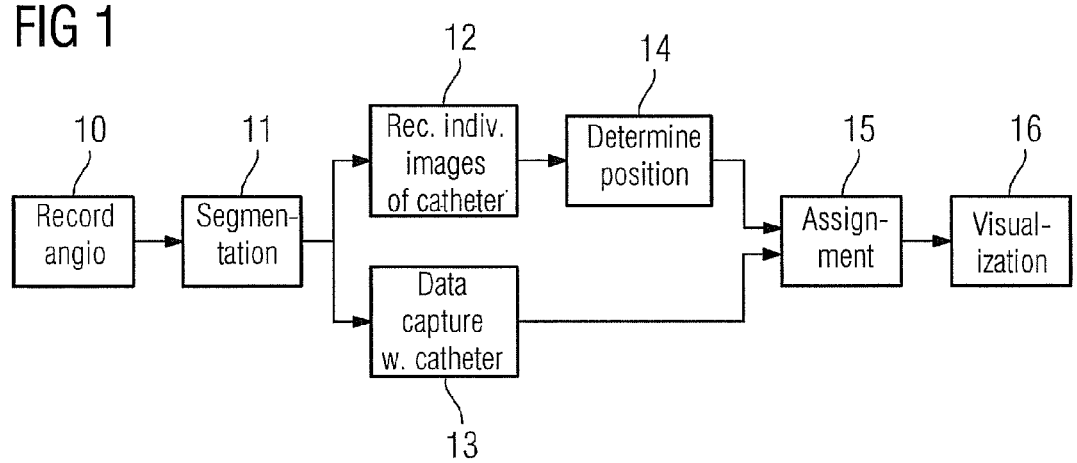
FIG. 1 a sequence of the steps of the inventive method.
Figure 2:
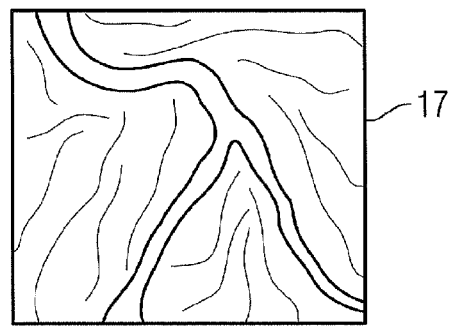
FIG. 2 a view of an angiography dataset of a vascular system.

FIG. 1 shows a sequence of steps of the inventive method. In a first step 10 an x-ray image dataset, especially an angiography sequence of a hollow organ (e.g. vascular system), which is to be examined is recorded or made available from a memory. Such an angiography dataset 17 with a hollow organ is shown in FIG. 2. Subsequently the hollow organ is interactively segmented in a second step 11. This step is optional. If more than one hollow organ is imaged in the x-ray image dataset the corresponding hollow organ to be examined can first be identified and then segmented. The x-ray image dataset with the segmented hollow organ is used later as an anchor point of the registration of the datasets of the data capture unit (e.g. IVUS). The x-ray image dataset can be produced and triggered or also triggered for example by organ movements such as the heartbeat, especially EKG-triggered. At the time of recording of the x-ray image dataset there is preferably no catheter in the hollow organ.

In a third step 12 a series of individual x-ray images are recorded during the movement of a catheter through the hollow organ. The individual x-ray images are preferably registered with the x-ray image dataset so that overlaying and spatial assignment is possible. The individual x-ray images are recorded as a time sequence, so that the progress of the catheter through the hollow organ is mapped accordingly. The individual x-ray images can for example involve 2D fluoroscopy or angiography x-ray images. The catheter is embodied such that at least one part of the catheter, for example the tip, is not transparent for x-ray radiation so that the catheter is recognizable at least partly on the individual x-ray images.

Figure 3:
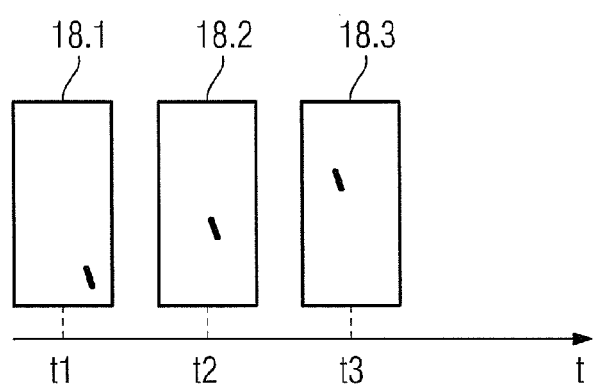
FIG. 3 a view of a sequence of individual x-rays during a movement of a catheter.

The individual x-ray images are each assigned time information, especially the time of recording relative to a randomly selected reference time. FIG. 3 shows a sequence of individual x-ray images 18.1; 18.2; 18.3 plotted along a time axis t, which is recorded at different consecutive times and on which the progress of the catheter can be recognized. The first individual x-ray image 18.1 was recorded at a first time t1, the second individual x-ray image 18.2 at a second time t2 and the third individual x-ray image 18.3 at a third time t3. The associated times are stored with the individual x-ray images.

Simultaneously with the third step a series of datasets is recorded in a fourth step 13 by means of a data capture unit arranged in or on the catheter. The datasets are likewise each assigned time information, especially once again the time of data capture relative to the corresponding reference time. FIG. 4 shows a sequence of datasets 19.1; 19.2; 19.3 of the data capture unit plotted along the time axis which were recorded at different consecutive times and on which for example images of the hollow organ walls can be seen. The first dataset was recorded at a first time t1, the second dataset at a second time t2 and the third dataset that a third time t3. The associated times are stored with the datasets.

The catheter or wire features an intravascular ultrasound imaging unit as the data capture unit for example. A so-called IVUS unit is especially suitable for imaging of vessel walls. A unit for optical coherence tomography or for lipid measurement or for pressure measurement (a so-called pressure wire) can also be provided however. A number of different data capture units such as IVUS and OCT or OCT and pressure measurement can also be present. The movement of the catheter is in general conducted as a withdrawal movement after moving the catheter into a distal position. The movement can in this case be carried out manually or automatically (pullback system). Alternately a forwards movement can also be carried out.

In a fifth step 14 the respective position of the catheter is determined on the basis of the individual x-ray images recorded. A specific image processing algorithm is used for this for example, for example an edge detection algorithm which identifies on the individual x-ray images the non-transparent part of the catheter for the x-ray radiation, obtains the location information from this and determines the position. This can for example be carried out with the aid of an image processing unit and/or a data-processing unit. In the event of organ movements and with the aid of a triggered image acquisition (e.g. EKG), an improved detection and recording of the location information can be provided.

In a sixth step 15 the datasets are then correlated on the basis of the time information with the individual x-ray images and thereby with the corresponding positions of the catheter. Thus the datasets and individual x-ray images recorded at the same times are determined and the corresponding datasets are assigned to the position determined for the corresponding position of the catheter. This can for example likewise be carried out by the image processing unit and/or the data-processing unit.

In a seventh step 16 the datasets and the x-ray dataset are then jointly visualized, for example overlaid jointly in a display unit or inserted next to one another, for example while a position marker is inserted within the displayed x-ray image dataset which specifies the position information of the respective dataset belonging to it. This is shown for example in FIG. 5 which shows a combined image. An angiography image dataset of a vessel system is shown here on the right hand side, with a position marker 30 marking a position of the vascular system, the vessel wall of the vascular system at this position is mapped to the left and to the bottom. The position marker can be moved either automatically or manually, when this is done the corresponding associated datasets are shown.

The inventive method can be carried out automatically and thus automatically display to a user a comprehensive visualization of the hollow organ.

FIG. 6 shows an example of a medical imaging system, consisting of an angiography x-ray system and a catheter system, which is suitable for carrying out the inventive method. A C-arm 23 designed as a holder for an x-ray source 21 and an x-ray detector 22 is arranged on an articulated-arm robot 24. The C-arm of the articulated arm robot enables the x-ray source and the x-ray detector to be positioned as required. At the same time a catheter 27 with a data capture unit 26 is present, which can be moved through the body, especially through the vascular system of a patient. X-ray images, especially also angiography images, can be recorded by means of the medical imaging system. The system is controlled by a control system 25, with two control units also able to be present, of which one controls the x-ray imaging and the other controls the catheter. The two control units can then preferably communicate with each other. In addition the medical imaging system has an image processing unit 28 and a display unit 29 for displaying the combined images.

The method can also include a combination of a number of different examination techniques (e.g. IVUS and OCT or OCT and pressure wire) and their synchronized visualization. Thus for example a catheter can record data with an IVUS unit and this process can be triggered by individual x-ray images, in addition OCT data capture can then capture data and this can be undertaken untriggered by individual x-ray images; subsequently the two examination techniques can be synchronized via position determination with each other and can be displayed jointly.

The inventive method includes the use of position and time information of the datasets of the data capture unit, e.g. IVUS, and the individual x-rays, e.g. angiography images. In this way an image-based co-registration of IVUS and angiography is achieved. Since the inventive method manages without the use of landmarks or a vascular model, it can be used both for manual and also for automatic pulling back of the IVUS catheter. The order of the steps of the inventive method can also be varied, provided the steps are not dependent on one another.

The invention can be briefly summarized as follows: For an improved visualization of hollow organ a method for visualization of hollow organs of a patient is provided, with the following steps:

Recording and registration of an x-ray image dataset of the hollow organ,

Recording of a number of individual x-ray images during a movement of an instrument with a data capture unit through the hollow organ, with each individual x-ray image featuring time information, Recording datasets of the data capture unit during the movement of the instrument, with each dataset featuring time information, Determining the position of the instruments on the basis of the individual x-ray images by means of an image recognition algorithm, Spatial assignment of the datasets of the data capture unit and the position of the instrument on the basis of the time information of the datasets of the data capture unit and the individual x-ray images, Joint visualization of the datasets of the data capture unit with the x-ray image dataset.

The invention claimed is:

1. A method for visualizing a hollow organ of a patient, comprising:
   recording an x-ray image dataset of the hollow organ by an x-ray system;
   recording a number of individual x-ray images of an instrument having a data capture unit during a movement of the instrument through the hollow organ by the x-ray system, wherein the individual x-ray images feature time of recoding the individual x-ray images;
   simultaneously recording datasets of the hollow organ by the data capture unit during the movement of the instrument, wherein the datasets feature time of recording the datasets;
   registering the individual x-ray images with the x-ray image dataset by an imaging processing unit;
   detecting positions of the instrument based on the individual x-ray images by the imaging processing unit, wherein the individual x-ray images are 2D fluoroscopy or angiography x-ray images;
   determining the datasets and the individual x-ray images having same time of recording;
   assigning the datasets recorded by the data capture unit with the individual x-ray images having the same time of recording so that the detected positions of the instrument based on the individual x-ray images are spatially assigned to the datasets by the imaging processing unit; and
   jointly visualizing the datasets recorded by the data capture unit with the x-ray image dataset by a display unit.

2. The method as claimed in claim 1, further comprising segmenting the hollow organ based on the x-ray image dataset.

3. The method as claimed in claim 1, wherein an angiography x-ray image dataset is recorded as the x-ray image dataset of the hollow organ is.

4. The method as claimed in claim 1, wherein the positions of the instrument are detected by an edge detection algorithm.

5. The method as claimed in claim 1, wherein the positions of the instrument are detected automatically.

6. The method as claimed in claim 1, wherein the recoding of the individual x-ray images or the x-ray image dataset is EKG-triggered.

7. The method as claimed in claim 1, wherein the instrument comprise a catheter.

8. The method as claimed in claim 7, wherein the catheter comprises a catheter tip not transparent to x-rays.

9. The method as claimed in claim 1, wherein the data capture unit comprises an imaging unit.

10. The method as claimed in claim 1, wherein the data capture unit is selected from the group consisting of: an ultrasound measurement unit, a pressure measurement unit, a lipid measurement unit, and an optical coherence tomography unit.

11. The method as claimed in claim 1, wherein the steps of the method is carried out automatically.

12. The method as claimed in claim 1,
   wherein the time of recoding the individual x-ray images is assigned to a reference time,
   wherein the time of recording the datasets is assigned to a corresponding reference time, and
   wherein the individual x-ray images are stored together with the datasets relative to a same reference time.

13. The method as claimed in claim 12, wherein the reference time and the corresponding reference time are randomly selected.

14. A medical imaging system for visualizing a hollow organ of a patient, comprising:
- an instrument having a data capture unit that captures datasets of the hollow organ during a movement of the instrument through the hollow organ, wherein the datasets feature time of recording the datasets;
- an x-ray system comprising an x-ray source and an x-ray detector that records an x-ray image dataset of the hollow organ and a number of individual x-ray images of the instrument during the movement of the instrument, wherein the individual x-ray images feature time of recoding the individual x-ray images;
- an image processing unit that:
  - registers the individual x-ray images with the x-ray image dataset,
  - detects positions of the instrument based on the individual x-ray images, wherein the individual x-ray images are 2D fluoroscopy or angiography x-ray images,
  - determines the datasets and the individual x-ray images having same time of recording, and
  - assigns the datasets recorded by the data capture unit with the individual x-ray images having the same time of recording so that the detected positions of the instrument based on the individual x-ray images are spatially assigned to the datasets; and
- a display unit that jointly displays the datasets recorded by the data capture unit with the x-ray image dataset.

15. The medical imaging system as claimed in claim 14, wherein the instrument comprise a catheter.

16. The medical imaging system as claimed in claim 15, wherein the catheter comprises a catheter tip not transparent to x-rays.

17. The medical imaging system as claimed in claim 14, wherein the data capture unit comprises an imaging unit.

18. The medical imaging system as claimed in claim 14, wherein the data capture unit is selected from the group consisting of: an ultrasound measurement unit, a pressure measurement unit, a lipid measurement unit, and an optical coherence tomography unit.

* * * * *